United States Patent [19]

Annen et al.

[11] 4,330,541
[45] May 18, 1982

[54] NOVEL CORTICOID 17-THIOACETALS, THEIR PREPARATION AND USE

[75] Inventors: Klaus Annen; Henry Laurent; Helmut Hofmeister; Karl Petzoldt; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 226,985

[22] Filed: Jan. 21, 1981

[30] Foreign Application Priority Data

Dec. 21, 1979 [DE] Fed. Rep. of Germany ....... 2952003

[51] Int. Cl.³ .............................................. A61K 31/56
[52] U.S. Cl. ............................... 424/243; 260/397.45; 260/397.47
[58] Field of Search ..................... 424/243; 260/397.45

[56] References Cited

U.S. PATENT DOCUMENTS 4,207,316  6/1980  Schottle et al. ...................... 424/243
4,224,320  9/1980  Dahl et al. ......................... 260/397.4

Primary Examiner—Elbert L. Roberts
Attorney, Agent, or Firm—Millen & White

[57] ABSTRACT

Novel corticoid 17-thioacetals of the formula:

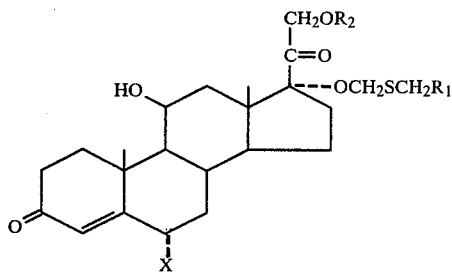

wherein
  X is hydrogen, fluorine or methyl,
  $R_1$ is hydrogen or $C_1$–$C_6$ alkyl, and
  $R_2$ is hydrogen or the acyl group of a $C_{1-16}$ - hydrocarbon carboxylic acid, have valuable medicinal properties, e.g., as antiinflammatories.

15 Claims, No Drawings

NOVEL CORTICOID 17-THIOACETALS, THEIR PREPARATION AND USE

BACKGROUND OF THE INVENTION

The present invention relates to novel antiinflammatory corticoids.

European Patent Application 0 003 341 (U.S. Pat. No. 4,207,316) discloses antiinflammatory corticoid 17-acetals and -thioacetals which, however, have properties in need of improvement.

SUMMARY OF THE INVENTION

Accordingly, it is an object of this invention to provide such improved corticoids.

Upon further study of the specification and appended claims, further objects and advantages of this invention will become apparent to those skilled in the art.

These objects have been attained by providing corticoid 17-thioacetals of the formula:

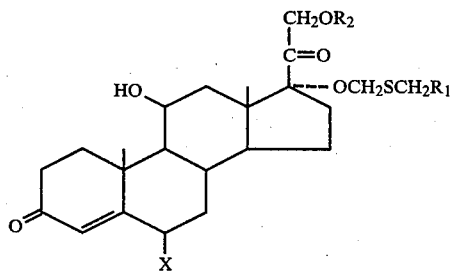

wherein
X is hydrogen, fluorine or methyl,
$R_1$ is hydrogen or a lower alkyl, and
$R_2$ is hydrogen or acyl.

DETAILED DISCUSSION

The corticoid 17-thioacetals of Formula I can have as X, a fluorine atom, a methyl group or a hydrogen atom. Corticoid 17-thioacetals are preferred which have a methyl group or, especially, a hydrogen atom as X.

As $R_1$, the corticoid 17-thioacetals can have a hydrogen atom or a lower alkyl group (e.g., of 1–6 carbon atoms). Lower alkyl groups are understood to mean preferably a group of 1–4 carbon atoms, e.g., methyl, ethyl, propyl, isopropyl, or butyl. Especially preferred are corticoid 17-thioacetals of Formula I having a hydrogen atom as $R_1$.

The corticoid 17-thioacetals of Formula I have as $R_2$, a hydrogen atom or an acyl group. Suitable acyl groups $R_2$ are those groups customarily utilized in the ester groups in the 21-position of corticoid molecules. Suitable acyl groups include, for example, groups of 1–16 carbon atoms derived from straight-chain or branched, saturated or unsaturated aliphatic mono- or dicarboxylic hydrocarbon acids which can be substituted as conventional to form equivalent acyl groups, for example, those substituted by hydroxy groups, amino groups, or halogen atoms.

Furthermore suitable as acyl groups are such residues as cycloaliphatic, aromatic, mixed aromatic-aliphatic, hydrocarbon or heterocyclic acids, which can likewise be substituted in the usual way. As can be seen, the nature of the acyl moiety is not critical and many alternatives are equivalent, e.g., the hetero acids are equivalent to the hydrocarbon hetero acids. Examples of such suitable acyl groups include: formyl, acetyl, propionyl, butyryl, pentanoyl, hexanoyl, octanoyl, undecanoyl, dimethylacetyl, trimethylacetyl, diethylacetyl, tert-butylacetyl, benzoyl, phenacetyl, cyclopentylpropionyl, hydroxyacetyl, monochloroacetyl, dichloroacetyl, trichloroacetyl, dimethylaminoacetyl, trimethylaminoacetyl, diethylaminoacetyl, piperidinoacetyl, nicotinyl, ω-carboxypropionyl, ω-carboxypentanoyl etc.

Preferred acyl groups $R_2$ are those of 1–8 carbon atoms and especially those derived from a straight-chain or branched alkanecarboxylic acid of 1–6 carbon atoms.

As mentioned, European Patent Application 0 003 341 discloses corticoid 17-acetals and corticoid 17-thioacetals. The corticoid 17-thioacetals of this invention have the advantage over these previously known, structurally analogous compounds in that they display, upon topical application, a stronger antiinflammatory activity and/or they exhibit a more favorable dissociation between desirable topical efficacy and undesirable systemic effect.

The topical efficacy can be determined as follows using conventional protocols such as the vasoconstriction test. This test is conducted on 8 healthy test subjects of both sexes who, during the preceding two weeks, had not received any local corticosteroid treatment. After removal of the stratum corneum down to the stratum lucidum on the tests subjects' backs (by pulling off adhesive tape 20–40 times), 0.1 g of a preparation is applied to areas of a size of 4 cm² without occlusive bandaging. To avoid applying the same preparation to identical skin areas, the application is made in a rotating fashion.

Vasoconstriction is evaluated visually after 4 hours and 8 hours by the investigator in accordance with the following effectiveness grading: 1=absolute fading: 2=minor residual erythema; 3=medium-grade erythema, reddening intensity in the medium range of stripped, untreated, and undamaged skin; 4=erythema with minor faded areas; 5=no fading or increase of erythema.

The individual evaluations are averaged.

In each test series, diflucortolone 21-valerate (=6α,-9α-difluoro-11α-hydroxy-16α-methyl-21-valeryloxy-1,4-pregnadiene-3,20-dione=DFV) is used as the reference compound.

In each case, a difference Δ is determined between the medium degrees of efficacy of DFV and the test compound as found in the individual series of experiments. Positive deviations Δ denote a more favorable evaluation of the test compound as compared with DFV; negative deviations show a less favorable evaluation.

The following table lists the test results observed when the test subjects are treated with a preparation containing 0.1 ppm of active agent.

The systemic activity of the compounds can also be determined using conventional protocols, e.g., the conventional skin tearing test as follows:

Male Wistar rats (weight 150±20 g) receive an application of 6 mg of test compound daily in 0.2 ml of "Cetiol" on the depilated skin of the back over a period of 20 days. A special plastic cover prevents the animals from licking off the applied compound. During the test, the body weight is controlled and, at the end of the test, the organ weight of the spleen is measured. The treated skin of the back is removed and prepared in a size of about 5×5 cm. The skin thickness is determined. From the piece of skin, two double-T-shaped strips are cut out with the aid of a steel punch. The skin strip is clamped with its broad ends into the pulling jaws of a special measuring device. Then the force is measured which is required for stretching and tearing the skin strip.

The following table demonstrates the test results obtained in this experiment.

| No. | Compound | Vasoconstriction Test Δ | | Weight of Animals | Skin Tearing Test | | Maximum Deformation |
| --- | --- | --- | --- | --- | --- | --- | --- |
| | | After 4 Hours | After 8 Hours | | Spleen Weight | Tear Strength of Skin | Resistance of Skin |
| I | 11β,21-Dihydroxy-17α-methoxymethoxy-4-pregnene-3,20-dione (Europ. Patent Appln. No. 3341) | +0.3 | +0.7 | −14% | −28% | −36% | −43% |
| II | 11β,21-Dihydroxy-17α-methylthiomethoxy-4-pregnene-3,20-dione | +0.9 | +0.9 | −7% | −15% | −7% | −8% |

The novel corticoid 17-thioacetals of this invention are suitable, in combination with the vehicles customary in galenic pharmacy, for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar skin diseases in mammals, including humans.

The medical specialties are prepared in the usual way by converting the active agents into the desired forms of application with suitable additives, e.g., solutions, lotions, ointments, creams, or plasters. In the thus-formulated medicines, the concentration of active compound is dependent on the type of application. In the case of lotions and ointments, an active agent concentration of 0.001% to 1% is preferably employed. Administration is as conventional with such topical formulations, e.g., as with a hydrocortisone cream.

Moreover, the novel compounds, optionally in combination with the customary vehicles and excipients, are also highly suitable for the preparation of inhalants usable for the therapy of allergic diseases of the respiratory tract, e.g., bronchial asthma or rhinitis. These can be administered analogously to the administration of the conventional inhalant beclomethasone dipropionate.

The novel corticoids are also suitable furthermore in the form of capsules, tablets, or dragees, containing preferably 10–200 mg of active agent and being administrable orally (e.g., at daily dosages of 0,2–20 mg/kg), or in the form of suspensions containing preferably 100–500 mg of active agent per dosage unit and being administered rectally (e.g., at a daily dosage of 0,2–20 mg/kg), for the treatment of allergic diseases of the intestinal tract, such as colitis ulcerosa and colitis granulomatosa analogously to the administration of the conventional such agent betamethasone disodium phosphate.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

The novel corticoid 17-thioacetals can be prepared according to the process summarized below under conventional conditions, e.g., those described in European Patent Application 0 003 541, whose disclosure is incorporated by reference herein.

A process for preparing corticoid 17-thioacetals of Formula I comprises conventionally (a) reacting a corticoid of Formula II

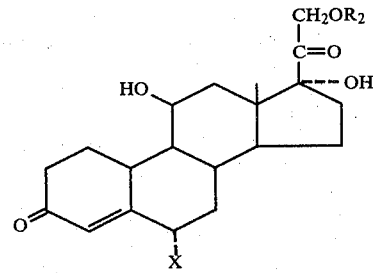

wherein X and $R_2$ are as defined above optionally after intermediary protection of the 11- and 21-hydroxy groups, with a sulfoxide of Formula III $CH_3SOCH_2R_1$ (III)

wherein $R_1$ is as defined above, and optionally saponifying a 21-ester group, if present, or esterifying a 21-hydroxy group if present; or (b) fermenting a steroid 17-thioacetal of Formula IV

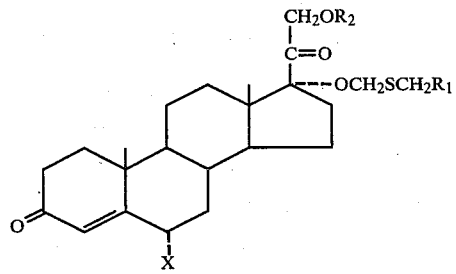

wherein X, $R_1$, and $R_2$ are as defined above optionally while simultaneously splitting off an existing 21-ester group, with a microorganism culture capable of 11β-hydroxylation, e.g., of the genus Curvularia, e.g., *Curvularia lunata*, and, optionally, esterifying any existing 21-hydroxy groups.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

21-Acetoxy-11β-hydroxy-17α-methylthiomethoxy-4-pregnene-3,20-dione (a) A solution of 5.0 g of hydrocortisone acetate in 25 ml of pyridine is combined dropwise at $-15°$ C. with 3 ml of trifluoroacetic anhydride and stirred for 10 minutes at $-10°$ C. The mixture is poured onto an ice water-sodium chloride solution, and the precipitate is filtered off. The residue is taken up in methylene chloride, washed neutral, and, after drying over sodium sulfite, concentrated under vacuum. Yield: 5.1 g of 21-acetoxy-17α-hydroxy-11β-trifluoroacetoxy-4-pregnene-3,20-dione.

(b) 3.7 g of the above crude product is agitated overnight in a mixture of 31 ml of dimethyl sulfoxide, 20.5 ml of acetic anhydride, and 6.2 ml of glacial acetic acid at room temperature. The reaction solution is poured onto a 10% sodium carbonate solution, and the precipitate is filtered off. The residue is dissolved in methylene chloride and worked up as usual after having been washed neutral. After chromatography on 600 mg of silica gel with a methylene chloride-acetone gradient (0–12% acetone), 3.48 g of 21-acetoxy-17α-methylthiomethoxy-11β-trifluoroacetoxy-4-pregnene-3,20-dione is isolated.

(c) 2.0 g of 21-acetoxy-17α-methylthiomethoxy-11β-trifluoroacetoxy-4-pregnene-3,20-dione is stirred at room temperature for 4 hours in 50 ml of methanol and 2.5 ml of triethylamine. The crude product is purified on 300 g of silica gel with a methylene chloride-acetone gradient (0–8% acetone), thus isolating 1.54 g of 21-acetoxy-11β-hydroxy-17α-methylthiomethoxy-4-pregnene-3,20-dione.

Melting point 167° C.
$[\alpha]_D^{25} = +160°$ (chloroform)
UV: $\epsilon_{241} = 16,100$ (methanol).

EXAMPLE 2

11β,21-Dihydroxy-17α-methylthiomethoxy-4-pregnene-3,20-dione 2.4 g of 21-acetoxy-17α-methylthiomethoxy-11β-trifluoroacetoxy-4-pregnene-3,20-dione is stirred overnight at room temperature in 50 ml of methanol and 3.0 ml of triethylamine. The crude product is purified on 350 g of silica gel with a methylene chloride-acetone gradient (0–12% acetone). Yield: 1.25 g of 11β,21-dihydroxy-17α-methylthiomethoxy -4-pregnene-3,20-dione.

Melting point 148° C.
$[\alpha]_D^{25} = +172°$ (chloroform)
UV: $\epsilon_{242} = 16,200$ (methanol).

EXAMPLE 3

11β-Hydroxy-17α-methylthiomethoxy-21-propionyloxy-4-pregnene-3,20-dione

Starting with 3.5 g of 11β,17α-dihydroxy-21-propionyloxy-4-pregnene-3,20-dione, analogously to the reaction sequence of 1(a)-(c), 920 mg of 11β-hydroxy-17α-methylthiomethoxy-21-propionyloxy-4-pregnene-3,20-dione is obtained.

Melting point 142° C.
$[\alpha]_D^{25} = +167°$ (pyridine)
UV: $\epsilon_{241} = 16,100$ (methanol).

EXAMPLE 4

21-Butyryloxy-11β-hydroxy-17α-methylthiomethoxy-4-pregnene-3,20-dione

Analogously to the reaction sequence of 1(a)-(c), 2.8 g of 21-butyryloxy-11β,17α-dihydroxy-4-pregnene-3,20-dione yields 780 mg of 21-butyryloxy-11β-hydroxy-17α-methylthiomethoxy-4-pregnene-3,20-dione.

Melting point 133° C.
$[\alpha]_D^{25} = +160°$ (pyridine)
UV: $\epsilon_{242} = 16,300$ (methanol).

EXAMPLE 5

11β-Hydroxy-17α-methylthiomethoxy-21-valeryloxy-4-pregnene-3,20-dione 1.2 g of 11β,21-dihydroxy-17α-methylthiomethoxy-4-pregnene-3,20-dione is stirred in 12 ml of pyridine and 6 ml of n-valeric anhydride for 17 hours at room temperature. After the reaction mixture has been worked up as usual and purified on 150 g of silica gel with a methylene chloride-acetone gradient (0–12% acetone), 987 mg of 11β-hydroxy-17α-methylthiomethoxy-21-valeryloxy-4-pregnene-3,20-dione is isolated.

Melting point 138° C.
$[\alpha]_D^{25} = +157°$ (pyridine)
UV: $\epsilon_{241} = 16,100$ (methanol).

EXAMPLE 6

11β-Hydroxy-17α-methylthiomethoxy-21-trimethylacetoxy-4-pregnene-3,20-dione

A solution of 1.6 g of 11β,21-dihydroxy-17α-methylthiomethoxy-4-pregnene-3,20-dione in 15 ml of pyridine and 8 ml of trimethylacetic anhydride is stirred overnight at room temperature. The mixture is worked up as usual, isolating after purification by chromatography 1.1 g of 11β-hydroxy-17α-methylthiomethoxy-21-trimethylacetoxy-4-pregnene-3,20-dione.

Melting point 175° C.
$[\alpha]_D^{25} = +158°$ (pyridine)
UV: $\epsilon_{242} = 16,200$ (methanol).

EXAMPLE 7

21-Acetoxy-11β-hydroxy-6α-methyl-17α-methyl-thiomethoxy-4-pregnene-3,20-dione 4.1 g of 21-acetoxy-11β,17α-dihydroxy-6α-methyl-4-pregnene-3,20-dione is reacted under the conditions of the reaction sequence of 1(a)-(c) to 1.7 g of 21-acetoxy-11β-hydroxy-6α-methyl-17α-methylthiomethoxy-4-pregnene-3,20-dione.

Melting point 189° C.

EXAMPLE 8

A 1-liter Erlenmeyer flask containing 200 ml of a nutrient solution sterilized for 30 minutes in an autoclave at 120° C. and consisting of 3% glucose, 1% corn steep, 0.2% NaNO₃, 0.1% KH₂PO₄, 0.2% K₂HPO₄, 0.05% MgSO₄.7H₂O, 0.002% FeSO₄.7H₂O, and 0.05% KCl is inoculated with a lyophilized culture of Curvularia lunata (NRRL 2380) and vibrated for 70 hours at 30° C. on a rotary shaker. Two 2-liter Erlenmeyer flasks are inoculated with respectively 50 ml of this germination culture, these flasks having been filled with respectively 500 ml of sterilized nutrient medium of the same composition as in case of the preliminary culture. After an incubating period of 6 hours at 30° C. on the rotary shaker, 100 mg of 21-acetoxy-17α-methylthiomethoxy-4-pregnene-3,20-dione dissolved in 0.5 ml of dimethylformamide is added under sterile conditions to each flask, and shaking is continued. The course of fermentation is controlled by the taking of samples, which are extracted with methyl isobutyl ketone and analyzed by thin-layer chromatography.

After a contact period of 64 hours, the substrate conversion is complete. The two flask contents are combined, the mycelium is removed by filtration, and the culture filtrate is extracted with methyl isobutyl ketone. The extract is evaporated to dryness under vacuum and the residue chromatographed over a silica gel column by means of the solvent gradient of methylene chloride-methylene chloride/acetone 7+3. The main fraction is concentrated to dryness and crystallized from acetone/-diisopropyl ether, thus obtaining 148 mg of 11β,21-dihydroxy-17α-methylthiomethoxy-4-pregnene-3,20-dione, melting point 149° C.

To prepare the starting compound, 1.5 g of 21-acetoxy-17α-hydroxy-4-pregnene-3,20-dione is reacted and worked up analogously to Example 1(b). After chromatography on 130 g of silica gel with a methylene chloride-acetone gradient (0–12% acetone), 1.28 g of 21-acetoxy-17α-methylthiomethoxy-4-pregnene-3,20-dione is isolated, melting point 149° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A corticoid 17-thioacetal of the formula

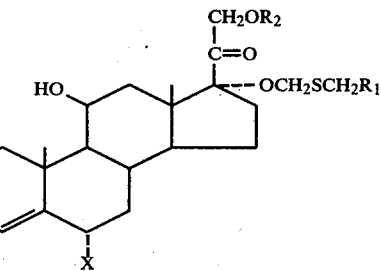

wherein
X is hydrogen,
R₁ is hydrogen or C₁–C₆ alkyl, and
R₂ is hydrogen or the acyl group of a C₁₋₁₆-hydrocarbon carboxylic acid.

2. A corticoid 17-thioacetal of claim 1, wherein R₁ is hydrogen.

3. A corticoid 17-thioacetal of claim 1, wherein R₂ is hydrogen or an acyl group of a C₁₋₈ hydrocarbon carboxylic acid.

4. 21-Acetoxy-11β-hydroxy-17α-methylthiomethoxy-4-pregnene-3,20-dione, a compound of claim 1.

5. 11β,21-Dihydroxy-17α-methylthiomethoxy-4-pregnene-3,20-dione, a compound of claim 1.

6. 11β-Hydroxy-17α-methylthiomethoxy-21-propionyloxy-4-pregnene-3,20-dione, a compound of claim 1.

7. 21-Butyryloxy-11β-hydroxy-17α-methylthiomethoxy-4-pregnene-3,20-dione, a compound of claim 1.

8. 11β-Hydroxy-17α-methylthiomethoxy-21-valeryloxy-4-pregnene-3,20-dione, a compound of claim 1.

9. 11β-Hydroxy-17α-methylthiomethoxy-21-trimethylacetoxy-4-pregnene-3,20-dione, a compound of claim 1.

10. A pharmaceutical composition comprising an anti-inflammatorily effective amount of a compound of claim 1 and a pharmaceutically acceptable carrier.

11. A pharmaceutical composition of claim 10, wherein the carrier is suitable for topical application.

12. A pharmaceutical composition of claim 10, containing two compounds of claim 1.

13. A method of treating inflammation in a host in need of such treatment comprising administering an antiinflammatorily effective amount of a compound of claim 1.

14. A corticoid of claim 1 wherein R₂ is hydrogen.

15. A corticoid of claim 1 wherein R₂ is acyl of a C₁₋₈ hydrocarbon carboxylic acid.

* * * * *